United States Patent [19]
Shah

[11] Patent Number: 5,571,567
[45] Date of Patent: Nov. 5, 1996

[54] DIP MOLDED POLYURETHANE FILM METHODS

[75] Inventor: Tilak M. Shah, Cary, N.C.

[73] Assignee: Polygenex International, Inc, Cary, N.C.

[21] Appl. No.: 478,931

[22] Filed: Jun. 7, 1995

Related U.S. Application Data

[62] Division of Ser. No. 158,604, Nov. 29, 1993.

[51] Int. Cl.$^6$ ......................................... B05D 1/18
[52] U.S. Cl. .................. 427/379; 427/385.5; 427/407.1; 524/104; 524/113; 524/233; 524/251; 524/315; 524/356; 524/376; 524/379; 524/385; 524/590
[58] Field of Search ..................... 524/590, 113, 524/104, 233, 356, 379, 385, 251, 315, 376; 427/379, 385.5, 407.1

[56] References Cited

U.S. PATENT DOCUMENTS

| | | | |
|---|---|---|---|
| 3,668,173 | 6/1972 | Wooster et al. | 524/726 |
| 3,896,753 | 7/1975 | Shepherd et al. | 524/548 |
| 4,301,053 | 11/1981 | Wolfrey | 524/906 |
| 4,431,763 | 2/1984 | Reed | 524/385 |
| 4,543,405 | 9/1985 | Ambrose et al. | 524/762 |
| 4,558,075 | 12/1985 | Suss et al. | 524/447 |
| 4,853,418 | 8/1989 | Hanada et al. | 524/591 |
| 5,254,619 | 10/1993 | Ando | 524/521 |

*Primary Examiner*—James J. Seidleck
*Assistant Examiner*—Rabon Sergent
*Attorney, Agent, or Firm*—Waldron & Associates

[57] ABSTRACT

Dip molding of thermoplastic polyurethane elastomers to form medical and surgical gloves, condoms, instrument and appliance covers, and other rubber goods is improved by a controlled viscosity, controlled rate of evaporation solvent system, including a strong polar solvent, a weak solvent or non-solvent to control viscosity, and a blush resistor to control the rate of evaporation and the effects of humidity. For particularly enhanced barrier film formation, a leveling agent is also included. One or more layers are dipped in sequential steps in thicknesses of 0.5 to 1.5 mils per layer, with complete integral film formation and substantially complete freedom from porosity and pin holes. Crosslinkable polyurethanes may be cured after fully molded.

10 Claims, 2 Drawing Sheets

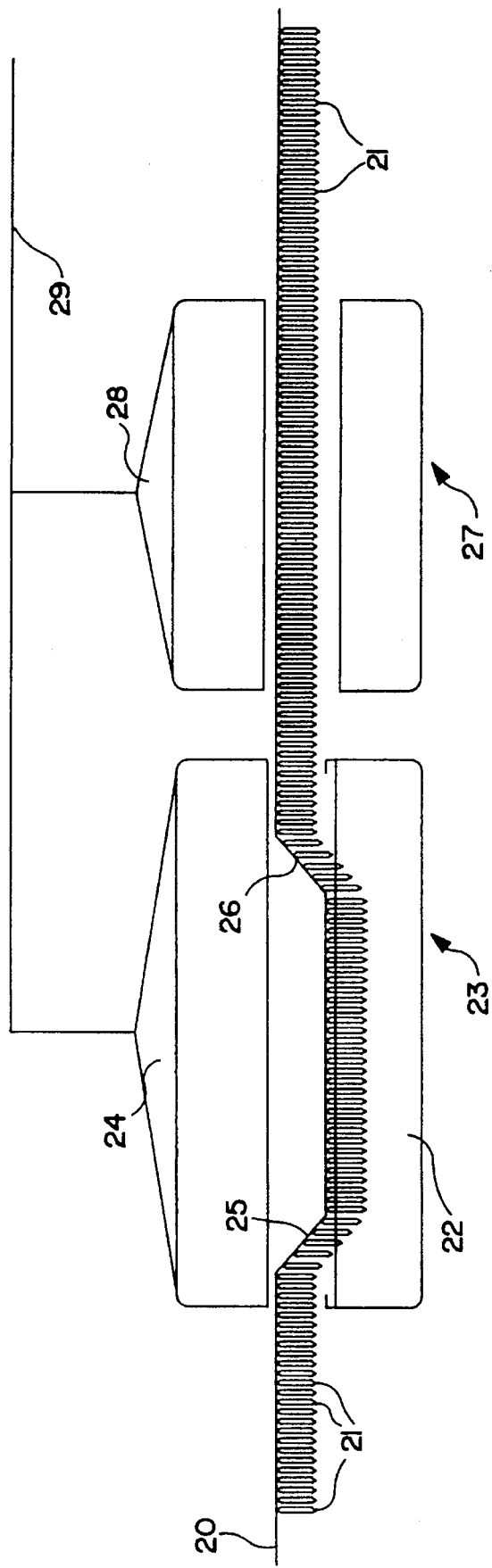

DIP MOLDED POLYURETHANE FILM METHODS

This is a divisional of application Ser. No. 08/158,604, filed Nov. 29, 1993.

TECHNICAL FIELD OF THE INVENTION

The present invention relates to the technical field of dip molded polyurethane products and to improved dipping compositions and methods. Dip molded polyurethanes are used for a wide variety of goods, such as medical and surgical gloves, condoms, cervical diaphragms and cervical caps, coverings for medical and electronic instruments and implements, and other fields where barrier films of a particular conformation are required.

BACKGROUND

Rubber goods and polymer barrier structures have long been employed, commonly formed of natural rubber (latex rubber) films formed by dip molding. A variety of problems beset the natural rubber products, including the occurrence of dermatitis, allergenic reactions, and anaphalactic shock reactions among people who work with or are subjected to exposure to latex products. In addition, latex rubber goods, and particularly dip molded latex rubber goods, have a substantial porosity with dimensions on the general order of the size of virus particles; when stretched in use, the pore dimensions are enlarged. The barrier effectiveness of latex rubber films and sheets is rather less than optimum.

In recent times, these problems have led to the employment of synthetic polymer elastomers in the fabrication of such rubber goods. The results have been good in many cases, but at a considerable price. Such products are normally formed from far more expensive polymers, and from dipping solutions in organic solvents which are also expensive, both in terms of materials costs and in handling requirements for environmental protection and safety considerations. In addition, the problems of quality control and uniformity of such products have not been fully and satisfactorily resolved, as pin holes and porosity remain common. Such products are little improved and generally far more expensive to produce. The potential benefits of employing synthetic polymer elastomers are only partly realized.

Among the elastomers employed in such production have been the class of thermoplastic polyurethane elastomers and cross-linked polyurethane elastomers. Polyurethanes offer very attractive properties for rubber goods but these benefits have not been fully and cost effectively realized.

Difficulties in dip molding of thermoplastic polyurethane elastomers include the following specific problems:

Solvents for thermoplastic polyurethane elastomers are highly polar organic solvents, typically tetrahydrofuran (THF), dimethyl acetamide (DMAC), dimethyl formamide (DMF), methyl ethyl ketone (MEK) and methylene chloride (MC), used alone or in blends. The polymers are dissolved slowly with heat and/or mixing, typically at polymer concentrations of about 3 to 7 weight percent.

The viscosity of the solution is directly proportional to the polymer concentration in such solutions, and can be increased or decreased by decreasing or adding, respectively, the proportion of the solvent.

At high viscosity, the formation of continuous films of the polyurethane is assured, but high viscosity also results in the formation of thick films which have other difficulties, particularly in the drying stage, as discussed below.

If the polymer concentration is reduced by adding additional solvent, film continuity suffers, with increasing proportions of pinholes, discontinuities and other film defects.

Balancing polymer concentration against viscosity is a quite difficult aspect of polyurethane dip molding, and is often made more complex by the additional considerations discussed hereafter.

The solvents effective for thermoplastic polyurethane elastomers did molding solutions are very highly volatile. Since the solvent is to be removed by evaporation, such a property is often considered a desirable attribute but, in practice, the effective range of solvents have proved to be excessively volatile, and introduce additional problems.

In most cases, the rapid evaporation of the solvents results in the formation of a thin surface film or crust of gelled or solidified polymer, with a substantial proportion of the solvent entrained within the depth of the film. The entrained solvent is evaporated from the polymer at a very slow rate, even at relatively high drying temperatures, and complete removal of the solvent is rarely attained.

One result of solvent entrainment is the solvent plasticizing of the polymer, altering the polymer properties for which the thermoplastic polyurethane elastomers is employed. The entrained solvent reduces the Vicat softening temperature, reduces elongation at break and tensile strength, and reduces the cut and puncture resistance of the film. Other properties of the polymer film are degraded as well.

Rapid evaporation of the solvent also serves to prevent "leveling" or coalescence of the polymer during the film formation, resulting in an unwelcome population of pin holes and other discontinuities which limit the barrier film properties of the material.

It is common to dip mold in multiple dipped layers in the formation of barrier film materials and products to overcome the incidence of pinholes. When multiple layers are dipped sequentially, the thin surface film and high levels of entrained solvent in an earlier layer can result in blistering and bubbling between the layers, introducing another form of discontinuity in the film.

The entrainment of solvents can also result in blushing and bleeding of the solvent at the surface of the film over time; for many uses, such properties are inappropriate and limiting. For implantable uses within the body, such bleeding is intolerable.

The crusting over of the film and the entrainment of solvents imposes a requirement for excessively long and expensive drying to remove as much of the solvent from the molded product as possible.

When the thermoplastic polyurethane elastomers is cross-linkable or curable, the significant levels of solvent entrained in the film can retard or inhibit the post forming reactions, resulting in an inferior cure of the polymer film.

The combination of high viscosity and high volatility of the dipping solutions combine to constrain the nature and amounts of ancillary compounding ingredients that can be employed in the films molded by such techniques. Compounding additives typically increase the viscosity and reduce the flow properties of such solutions and limit the effectiveness of the dip molding operation as the amounts are increased.

The entrainment and subsequent bleeding of residual solvent from dip molded goods is and unacceptable property for medical implants and many rubber goods designed for employment within the body of patients during surgical procedures. These constraints have considerably limited the use of thermoplastic polyurethane elastomers in rubber goods intended for such uses.

The thermoplastic polyurethane elastomers dip molded rubber goods require more expensive materials that natural rubber latex film rubber goods, including the polymer and the solvents. Such thermoplastic polyurethane elastomer goods thus necessarily face a materials cost disadvantage. The highly desirable properties supposed to be available and the avoidance of the specific disadvantages of latex products would ordinarily offset the cost disadvantage for substantial numbers of uses. In practice, however, the thermoplastic polyurethane elastomers introduce other cost disadvantages in addition to the cost of materials.

The thermoplastic polyurethane elastomers are slow to dissolve in the solvents, and require additional processing equipment for forming the solutions. Latex forms of natural rubber do not require such operations. In addition, the efforts to remove the solvent from the dip molded films is quite time consuming. As a result, the dip molding operations are more labor intensive, capital equipment intensive, and production rate limited when the thermoplastic polyurethane elastomers are employed, compared to natural rubber latex.

As noted above, the balancing of the dip molding characteristics of the thermoplastic polyurethane elastomer solutions is quite demanding and difficult. It is common to see quality control losses in production of rubber goods from the thermoplastic polyurethane elastomers of 30 to 40% for demanding quality control specifications. Such losses stem from high levels of pin holes and other discontinuities, from excessively thick films, and other similar problems.

As a consequence, rubber goods molded of thermoplastic polyurethane elastomers have proved excessively expensive and have met with limited commercial success despite the considerable theoretical advantages to be gained by the employment of these materials.

OBJECTS OF THE INVENTION

It is an object of the present invention to provide improved dipping solutions of thermoplastic polyurethane elastomers.

Another object of the present invention is to provide improved methods of dip molding of rubber goods molded of thermoplastic polyurethane elastomers.

Still another object of the present invention is to provide rubber goods molded of thermoplastic polyurethane elastomers having superior properties.

SUMMARY DESCRIPTION OF THE INVENTION

Dip molding of thermoplastic polyurethane elastomers to form medical and surgical gloves, condoms, cervical diaphragms and caps, instrument and appliance covers, and other rubber goods is improved by a controlled viscosity, controlled rate of evaporation solvent system, including a strong polar solvent, a weak solvent or non-solvent to control viscosity, and a blush resistor to control the rate of evaporation and the effects of humidity. For particularly enhanced barrier film formation, a leveling agent is also included. One or more layers are dipped in sequential steps in thicknesses of 0.5 to 1.5 mils per layer, with complete integral film formation and substantially complete freedom from porosity and pin holes. Cross-linkable polyurethanes may be cured after fully molded.

In the present invention, improved dip molding solutions of thermoplastic polyurethane elastomers are provided, based on a dip molding polyurethane elastomer composition comprising:

A. a thermoplastic polyurethane elastomer;

B. a first solvent component which is at least one strong solvent for the polyurethane elastomer;

C. a second solvent component which is at least one non-solvent or non-polar or low polarity weak solvent for the polyurethane elastomer, wherein the second solvent component is freely miscible with the first solvent component;

D. a third solvent component which is at least one blush resistor which limits the rate of evaporation of the first solvent component and the second solvent component and which limits the absorption of water vapor into the composition;

wherein the polyurethane is homogeneously dissolved in the solvent to form a solution having a viscosity of from about 400 to about 800 cP.

In dip molding operations, the improved dipping solutions of the present invention result in an improved dip molding method, wherein A. a dipping solution is formed as indicated above;

B. dipping a form into the solution to wet the surface of the form;

C. withdrawing the form from the solution to deposit a coating of the solution on the surface thereof, the coating having a thickness of from about 0.5 to 1.5 mils;

D. drying the coating to form a continuous, non-porous solid polyurethane elastomer film having a thickness of from about 0.5 to about 1.5 mils on the surface of the form;

E. repeating steps B, C, and D until the continuous, non-porous solid polyurethane elastomer film has a desired thickness;

F. stripping the continuous, non-porous solid polyurethane elastomer film from the form.

As those of ordinary skill in the art will understand, when a functional structure to be protected by the molded thermoplastic polyurethane is employed as the dipping form, the film is left in place, and the stripping of the film from the form is omitted.

The result is significantly improved rubber goods molded of multiple layers of thermoplastic polyurethane elastomers, including rubber gloves, particularly medical examination and surgical gloves, male and female condoms, cervical diaphragms and caps, organ bags and containments for use in endoscopic surgery, catheter balloons and inflatable cuffs and collars, disposable barrier coverings for medical appliances and instruments, as biocompatible coverings or coatings on implantable medical appliances, such as heart pacemakers and pacemaker batteries, protective coverings for industrial equipment, particularly electronic and electrical equipment operating in demanding environments, all having superior properties, particularly barrier properties, stemming from substantial freedom from pin holes or other discontinuities in the thermoplastic polyurethane elastomer film, substantially complete freedom from entrained solvents, and, when molded in multiple layers, substantial freedom from blisters and delamination between layers.

BRIEF DESCRIPTION OF THE DRAWINGS

FIG. 2 is a stylized illustration of a dip molding line employing a number of dipping mandrels and illustrating the dipping procedures and equipment employed in the practice of the present invention.

DETAILED DESCRIPTION OF THE INVENTION

Figure 1E:
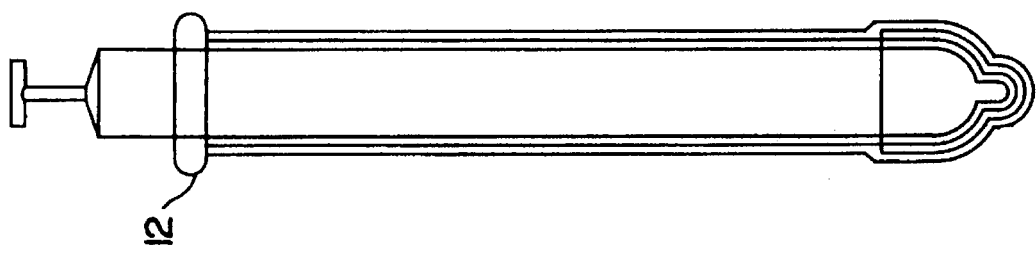
FIG. 1 is a stylized illustration of dipping mandrels at the several stages of dip molding articles in multiple layers in accordance with the present invention.

The term "rubber goods" as employed in the present invention refers broadly to the class of articles formed of elastomers in shapes and configurations suited for particular uses, as consumer goods, as industrial products, and particularly as medical and surgical products. Typically, such articles are relied upon, at least in part, for their barrier properties to isolate a person or a device from infectious diseases, from toxic materials, from corrosive or harmful environments, and the like. By way of illustration and not limitation, representative examples of such rubber goods include rubber gloves, particularly medical examination and surgical gloves, male and female condoms, cervical caps and diaphragms, organ bags and containments for use in endoscopic surgery, catheter balloons and inflatable cuffs and collars, disposable barrier coverings for medical appliances and instruments, as biocompatible coverings or coatings on implantable medical appliances, such as heart pacemakers and pacemaker batteries, protective coverings for industrial equipment, particularly electronic and electrical equipment operating in demanding environments.

In the context of the present invention, such rubber goods are made by dip molding of thermoplastic polyurethane elastomers, and may optionally be cross linked and cured after forming from such thermoplastic polyurethane elastomers.

In the present inventions, there are improvements provided in the dip molding solutions of the thermoplastic polyurethane elastomers, in the procedures and methods employed in dip molding the thermoplastic polyurethane elastomers, and in the rubber goods molded of thermoplastic polyurethane elastomers. All these improvements are interrelated and interdependent, and stem from a common objective.

The thermoplastic polyurethane elastomers to be employed in the present invention may be selected from the commercially available materials having physical and chemical properties suited to the intended use. A wide variety of such materials are available to those of ordinary skill in the art, and the selection of particular thermoplastic polyurethane elastomers does not itself form a part of the present invention. Many thermoplastic polyurethane elastomers are available in medical and/or food grades suitable for use in contexts which demand such characteristics.

Typically the polymers employed as the thermoplastic polyurethane elastomers in the present invention will be aliphatic polyurethanes, although aromatic polyurethanes may be employed as well, in cases where the requirements of use indicate the use of such a material.

The thermoplastic polyurethane elastomers are generally polymers formed by reacting di-isocyanates with diol or polyol groups of compounds or low molecular weight oligomers or polymers, frequently of polyesters or polyethers combined with aliphatic diol chain extenders, to form high molecular weight polymers. The properties and characteristics of such polymers are generally available in product literature from the producers of such materials, and those of ordinary skill in the art will be able to make appropriate selections for particular uses from the available information to suit the requirements of their particular uses. Among the important properties of such polymers is the fact that most are hypoallergenic, and a number are approved for medical use.

A variety of cross-linking methodologies are available for such polymers, including covalent cross-linking reactions based on reaction of the polymer reactive moieties with cross-linking agents, RF cross-linking, UV or visible light cross linking, X-Ray cross linking, and the like. The present invention may be employed with any of the commonly employed systems. As those of ordinary skill in the art will readily understand, it is appropriate to select a cross-linking system appropriate for the chosen polymer and end use or, less commonly, to select a polymer compatible with a selected cross-linking technique.

The material required for cross-linking of the thermoplastic polyurethane elastomers in the present invention can be dissolved or dispersed in the dipping solution. It will be preferred to avoid activation of the cross-linking reaction, by whatever technique, until after the dipping and solvent removal from the dip molded thermoplastic polyurethane elastomers is complete.

A key parameter in the present invention is the solvent system in which the thermoplastic polyurethane elastomers are dissolved. The solvent system is made up of:

a first solvent component which is at least one strong polar solvent for the polyurethane elastomer;

a second solvent component which is at least one non-solvent or non-polar or low polarity weak solvent for the polyurethane elastomer, wherein the second solvent component is freely miscible with the first solvent component; and a third solvent component which is at least one blush resistor which limits the rate of evaporation of the first solvent component and the second solvent component and which limits the absorption of water vapor into the composition.

The solvent system may contain, optionally, a leveling agent, an antifoaming agent, and other additives commonly included in such dip molding solutions. The use of such optional constituents may be preferred in particular cases and circumstances.

Strong solvents for the thermoplastic polyurethane elastomers employed in the present invention are generally highly polar organic liquids. Those most commonly employed include tetrahydrofuran (THF), N-methylpyrrolidone (NMP), dimethyl acetamide (DMAC), dimethyl formamide (DMF), methyl ethyl ketone (MEK) and methylene chloride (MC), and in most cases, one of these, or blends of two or more will be preferred for use as the strong solvent as defined herein.

The viscosity of the thermoplastic polyurethane elastomer solutions is controlled by the inclusion in the solvent system of one or more weak thermoplastic polyurethane elastomer solvents and/or one or more thermoplastic polyurethane elastomer non-solvents freely miscible with the strong solvent. Weak solvents and non-solvents for the polyurethanes are volatile organic liquids which are not highly polar, or which are non-polar. The role of these materials is to serve as viscosity controls in the solution without added solvency of the polymer.

While it would certainly be possible to produce solutions of the desired viscosity for the present invention with only strong solvents, the polymer solids content would be too low for reliable film formation, and the products would have too high a proportion of discontinuities, pin holes and pores in the film. In addition, the film would entrain very substantial proportions of the solvent as the film is dried.

The non-solvent or weak solvent permits the employment of appropriate levels of polymer solids in the solution at acceptable viscosities, and permits substantially complete removal of the solvent components from the film.

Suitable non-solvents for the thermoplastic polyurethane elastomers in the present invention include non-polar liquids, including aliphatic and aromatic hydrocarbons, and the like, having solubility parameters remote from that of the polymer, typically less than about 4.3, and preferably less than about 4.0 or greater than about 5.3, and preferably greater than about 5.5.

Suitable weak thermoplastic polyurethane elastomer solvents which may be employed include weakly polar liquids, including aliphatic alcohols, aliphatic amines, and the like.

As a preferred species, n-butanol is an effective diluent.

A blush resistor component is also added to the solvent system. Blush resistors are volatile organic liquids which are non-solvents or weak solvents for the thermoplastic polyurethane elastomers which operate to retard the rate of evaporation of the solvent system to a rate which prevents the formation of a thin surface film of solid polymer with solvated polymer trapped beneath.

While it has generally been the practice in the art to remove the solvent from the dipped coating in the most rapid fashion possible in order to speed production of rubber goods molded of thermoplastic polyurethane elastomers, we have found that overall productivity is greatly enhanced if the evaporation of the solvent and the drying of the film proceed at deliberately slower rates which prevent skinning of the surface of the dipped coating and the attendant entrainment of solvent. A boiling point of about 20° C. to 225° C. is generally effective, and a boiling point of about 100° C. to 200° C. is preferred.

Suitable materials to control the volatility of the solvent system include glycol ethers and esters and the like. Butyl Cellosolve (ethylene glycol monobutyl ether) having a boiling point of 171° C. is particularly preferred.

Leveling agents for the thermoplastic polyurethane elastomers are compounds which promote uniform flow of the solution and coalescence of the polymer film as the polymer comes out of solution when the solvent system is removed by volatilization from the deposited solution coating. In the thin layers employed in the present invention, such leveling agents are a preferred component of the solution. The increased coalescence serves to make the thickness of the solution coating more uniform in thickness and to minimize the formation of pin holes.

In the present invention, poly (dimethyl-siloxane) with a molecular weight of about 250 to about 1,000 is a preferred leveling agent.

These agents operate by reducing surface tension in the solution to promote uniform solution flow properties and promoting coalescence and cohesiveness of the polymer by functioning as a tackifier while the solidifying polymer is still solvent plasticized.

When silicone fluids and the like are employed as leveling agents, they also function to inhibit foaming of the solution, and tend to minimize the entrainment of bubbles of air in the dip coated solution film. This function promotes the integrity and uniformity of the dip molded film formed in the present invention.

The controlled viscosity of the did molding solution of the present invention permit relatively high solids content of the dissolved thermoplastic polyurethane elastomers in the solution. The polymer may be from about 6 to 12, and preferably about 8 to 10, percent by weight of the dip molding solution.

The solvent system will contain a major proportion of the first, strong solvent component, typically about 60 to 80 weight percent of the solvent blend. The balance will be the second, weak or non-solvent diluent, added in an amount sufficient to produce the required viscosity, typically about 15 to about 30 weight percent, and the blush resistor added in a an amount sufficient to retard volatility of the solvent blend by an effective degree to assure that the solvent is all removed during drying. A typical proportion for butyl cellosolve is about 6 to 10 weight percent.

The leveling agent will generally be employed in minor amounts, on the order of 0.1 to 1.0 weight percent of the solution.

The viscosity of the dipping solution of the present invention will be from about 400 to 800 cP. Higher viscosity makes it very difficult to achieve controlled and uniform film thicknesses and effective drying without solvent entrainment. Lower viscosity solutions do not build adequate film thickness, requiring additional layers to achieve a designed film thickness, and may form discontinuous films.

Through the use of the blush resistor to achieve low evaporation rates and to inhibit water absorption in the solution and the forming polymer film, it is possible to achieve a highly controlled film formation, and to substantially eliminate blushing, enhance coalescense of the forming film to prevent pin holes, cratering and discontinuities and, taken in combination with a suitable surfactant, reduce the formation of Benard cells or defects caused by exposure to air currents at the forming film surface. When multiple layer dipping is employed, as discussed infra, the blush resistor also serves to enhance interlayer adhesion without causing bubbling and/or blistering of the prior layers.

The low viscosity of the dip molding solution and the use of the leveling agent combine to afford exceptionally uniform film thickness and freedom from pin holes and other forms of discontinuity.

The advances in the formation of the dip molded films of the present invention permit a wider range of compounding ingredients and their proportions than has previously been the case in dip molding. All the ingredients usual to formulating the thermoplastic polyurethane elastomers may be employed in the context of the present invention, including some not ordinarily formulated into dip molding solutions.

Reinforcing fillers and inert diluent fillers may be employed in proportions up to about 25% by weight of the polymer. Such fillers, which may include carbon black, silica, and the like, as those of ordinary skill in the art will readily apprehend, can result in material improvement and enhancement of some of the physical properties of the thermoplastic polyurethane elastomers.

Pigments, dyes, lakes, opacifiers, optical brighteners, and the like may also be employed to provide a wide range of colors and other optical properties. Titanium dioxide, zinc oxide, and other particulate optical ingredients can be dispersed in the solution in suitable amounts. Soluble materials in the solvent system can be dissolved in suitable amounts. Such components can be present in the solution at levels of up to as much as about 5% by weight of polymer in the the dip molding solution.

When required, radiopaque pigments, such as lead particles, lead oxide, barium sulfate, bismuth subcarbonate, bismuth trioxide, bismuth oxychloride, and the like can be formulated into the dip molded articles by inclusion in the dip molding solution. Such radiopaque pigments make the molded articles detectable by X-Ray, and in higher proportions provide at least partial shielding to protect the user of the article. Full protection and shielding from X-Ray exposure will generally require additional protective measures however, as the shielding afforded in the present invention will generally be only partial. Such ingredients can be an important aspect of medical and surgical gloves, and for implantable devices or surgical implements such as catheter balloons, for example.

Antioxidants and ultraviolet stabilizers are frequently desirable additions to the formulations, as such ingredients can serve to substantially extend the service and shelf life of dip molded rubber goods molded of thermoplastic polyurethane elastomers.

Suitable biocides, biostats, flavors, fragrances and deodorants for use in the thermoplastic polyurethane elastomers may also be included in minor amounts, typically up to about 2% by weight of the polymer.

A wide variety of plasticizers are known for the thermoplastic polyurethane elastomers as a class. Such materials are not commonly employed in dip molded rubber goods of thermoplastic polyurethane elastomers, however, as the products are usually solvent plasticized in the normal techniques of formulation. The plasticizing effect is often dissipated over time as the solvent bleeds from the molded article, and can result in an unacceptable degree of variability in the properties of the material over time. In the present invention, the substantially complete removal of the solvent system during drying makes for a far more stable product over time, and also admits of the use of a minor proportion of plasticizers.

In dip molding the operations involved are relatively simple and straight forward procedures. The dipping solution is formed, as discussed above, a form or mandrel having the required shape and dimensions is dipped into the solution, withdrawn, and the solvent system is evaporated to leave the mandrel coated with a thin film of the polyurethane. When thicker films are required, which is typically the case, multiple dipping and drying steps are conducted in a cyclic operation until the required thickness of the film is attained. The film is then stripped from the form or mandrel.

In practice, the quality of the dip molded rubber goods formed by dip molding procedure are affected by a number of variables which must be controlled to establish and maintain uniform conditions and high quality in the products produced. In the practice of the present invention, the make up of the dipping solution, as described above is the focal starting point, but the best results require control of the following characteristics during the dipping operations:

The viscosity must be maintained at a uniform value within the range of 400 to 800 cP. Within that range, the higher the viscosity, the thicker will be the film produced, within the range of from about 0.5 to 1.5 mils. It is quite important to employ a uniform value to produce a uniform film thickness, all other conditions being equal. The solution viscosity is readily and conveniently adjusted by controlling the proportion of the second solvent component, the weak solvent or non-solvent. It may be convenient to make up the solution at a slightly higher viscosity than desired to facilitate letting down the solution with addition of the second component under the actual conditions of the molding operation.

A uniform temperature is also important, as the thickness and integrity of the film will vary with temperature. The solution temperature has a direct influence on the thickness of the solution coating deposited on the surface of the mandrel or form during the dipping operation, and particularly on the initial rate of solvent evaporation during the drying phase of the method. The appropriate temperature will vary with the selection of the strong solvent. Best results with dimethyl acetamide will be realized at elevated temperatures, on the order of about 50° to 70° C., most often about 55° to 65° C. THF and methylene chloride generally perform best at controlled temperature near ambient, but care must be taken as ambient conditions vary to maintain a constant temperature to avoid variations in the product properties.

The polymer concentration in the solution must be maintained at uniform levels as well, as significant variations can result in varying film thicknesses. Since the uptake of the polymer may be at a different rate from the withdrawal of solvent, and since the solvent will gradually evaporate from the dip bath, it will generally be necessary to monitor the polymer concentration and make periodic adjustments during operations. The solution will preferably be mixed to avoid concentration gradients within the dipping bath.

The forms or mandrels require more than the proper shape to produce the rubber goods. The forms must also be immersed at a temperature compatible with the dipping solution and additionally be surfaced with a non-stick material or be coated with a mold release agent to permit stripping of the molded product after drying. When a mold release agent is employed it should be a material not appreciably soluble in the solvent system to avoid accumulations of the material in the solution over time.

Inserting and withdrawing the form into and out of the dipping solution plays an important role in controlling the thickness of the film. The insertion must be slow enough to avoid splashing and the formation of significant waves in the solution, and rapid enough to facilitate productivity.

The dwell time of the form in the dipping solution bath is not narrowly critical, but it is important to assure that the surface of the form or mandrel is fully wet by the solution before the withdrawal is commenced. After insertion, a pause of a few seconds before the withdrawal is commenced is generally suitable.

The more significant parameter is the rate of withdrawal of the form from the solution. The solution will exhibit syneresis proportional to the solution surface tension which will tend to draw the solution from the form as it is withdrawn, thinning the deposited solution coating. For any given system, there will be an optimum rate for a particular targeted film thickness. The rate of withdrawal should be maintained at or near the optimum rate, which is readily determined within a few iterations of the operation.

As discussed above, one important function of the third, blush resistor component of the dipping solution is to retard the rate of evaporation of the solvent system. The purpose of the retardation is to limit or prevent the formation of a surface skin on the solution which would cause, if formed, entrainment of a substantial proportion of the solvent within the depth of the film.

In a seeming contradiction, the time period required for drying is actually reduced. The apparent paradox is resolved when it is understood that while the rate of evaporation is retarded, the rate of transport of solvent to the surface of the forming film is not, permitting substantially more complete volatilization of the solvent rather than the entrainment within the film, with very slow migration to the surface thereafter. A significant gain in productivity is the usual net result.

The drying temperature must be above the flash point of the blush resistor (the highest boiling point component of the solvent system), and below the Vicat softening temperature of the polymer. If a cross-linking system is employed which is thermally activated, it may be preferred to keep the temperature of the drying operation below the activation temperature to retard the cure until after the solvent is substantially completely removed from the film. Within these broad parameters, the temperature may be varied rather freely, although the rate of solvent removal is generally directly proportional to temperature, and most rapid at the highest permitted temperature.

Drying is continued until the solvent components are substantially completely removed.

Since the solvent system may include hygroscopic constituents, it is preferred, if possible to maintain a controlled, preferably low, humidity atmosphere during the drying operation. Low humidity is also an aid to the capture and recovery of the organic solvent components, which will normally be required and desirable. The lower the humidity, the more readily will the solvents be prepared for recycling and reuse in the procedure.

The removal of the solvent system from the forming film may be done at reduced pressure to accelerate the procedure if the equipment can be made available.

As the solvent is removed, the polymer precipitates from the solution in a gradual bulk process rather than forming a solid skin of the surface. This is a material aid to the transport of solvent from the solution to the exposed surface and results in far more rapid and complete volatilization of the solvent components.

As the solvent is removed, the solution grows increasingly viscous and tends to coalesce into a continuous coherent film substantially free of pin holes and discontinuities. In addition, the progressive transport of solvent to the exposed surface prevents the formation of localized concentrations of solvent which can form bubbles or pin holes during the drying operation. The quality of the rubber goods is, as a result, far better in the present invention than has commonly been achieved with the thermoplastic polyurethane elastomers.

The films formed in the present invention are from about 0.5 to about 1.5 mils in thickness. When thicker films are required, the present invention takes advantage of the properties of the dip molding solution and the dip molding process in particular fashion to attain still greater improvement in the quality of the rubber goods produced. In particular, while even single layers are remarkably low in the incidence of pin holes and pores, multiple layers afford even greater protection from such defects. Since most rubber goods molded of thermoplastic polyurethane elastomers require a film thickness greater than 0.5 mils, multiple layers will be the preferred and usual for of the products produced in the present invention.

In the present invention, multiple layers are formed of the entire structure of the product, or of selected portions thereof, by multiple dipping operations without concern for the occurrence of delamination, blistering or bubbling of the interface between layers, a common problem for the procedures of the prior art. In substantially eliminating the entrainment of solvent within the polymer, the source of such problems and difficulties is also eliminated. The superior flow and leveling properties of the dipping solutions of the present invention provide exceptionally uniform and controlled film thickness.

While multiple dipping operations have been attempted in the past, they have not met with success and are not in general commercial use in the production of rubber goods. The long understood theoretical capability of overlayering pinholes and producing defect free dip molded rubber goods has not been successful because of bubbling, blistering, a general lack of uniform and controlled film thickness, and the attendant losses of substantial proportions of the product to quality control defects. Such techniques have proved to be uneconomic and latent defects in the molded rubber goods have proved such products unacceptable for many uses.

Through the employment of selective multiple dipping operations, unique versions of such products can be produced in the present invention, as discussed in detail below. Substantially any required film thickness can be built of multiple layers in increments of from about 0.5 to about 1.5 mils. Each layer will be formed integrally with the preceding layer, to form a monolithic film without a readily detectable interface.

The integrity of the original layer or layers is not disrupted by subsequent dipping operations, as the level of available strong solvent is not available in the dipping solutions of the present invention which might redissolve the polyurethane. The strong solvent is substantially all associated with the dissolved thermoplastic polyurethane elastomer in the solution. There is little or no free solvent available to attack the previously formed film surface. The level of solvent is sufficient to cause each layer to solvent weld to the preceding layer, however, to form a tightly bonded structure.

Multilayer films built in accordance with the present invention have improved tear strength and elongation at break than a single dipped layer of comparable thickness. The multilayer films are assured of unparalleled freedom from pin holes and other discontinuities, resulting in greatly enhanced product yields.

The demands of most rubber goods will require film thicknesses greater than a single layer of film produced in accord with the present invention, so that multilayer dip molding is the usual and preferred form of the present invention. In such circumstances, it is generally possible in the present invention to produce dip molded rubber goods free of detectable pin holes and discontinuities (100% integrity) with reject rates of less than 10%, often less than 5%, compared to the usual reject rate for barrier layer products of 40% or more. The economies resulting from such high levels of productivity more than offset the multiple dipping complexities.

It is a major advantage of the present invention that the improved dipping solutions and the improved dipping method can be employed with existing dipping lines, and do not require additional or different equipment of facilities. Any existing dipping line and the existing equipment can be readily adapted by those of ordinary skill in the art to practice and optimize the present invention with the guidance provided in the present disclosure.

A rolled and solvent welded rim may be formed on the dipped product in the usual fashion to stabilize the edges of the molded structure. It is preferred that the rolled rim be formed after dipping the last layer, during the drying step while the polymer is still tacky to facilitate the solvent welding. The dipped product may be joined with other structures and elements by solvent bonding and dip coating techniques to form composite structures to shape and reinforce specific regions of the dipped article. Such procedures are discussed in more detail below.

After the dip molded product is produced, the post-forming operations usual in the art may be followed in customary fashion.

As noted above, cross-linking reactions, when employed, may be initiated during the drying operation but are generally deferred until the dip molding operation is complete and initiated afterward.

Surface additives may be applied, including lubricants, skin emollients, biocides, spermicides (which may be employed with condoms and cervical diaphragms and caps), powders, such as talc and corn starch (often employed with medical and surgical gloves, for example) and the like. Such materials and their uses are familiar to those of ordinary skill in the art and do not themselves for a part of the present invention.

The products may be stripped from the forms or mandrels by rolling or by eversion, or a combination of both, in the fashion usual in the art.

The molded products may be sterilized, if required, and packaged in the usual and customary forms known to the art.

As previously discussed, a wide variety of rubber goods molded of thermoplastic polyurethane elastomers can be produced as a part of the present invention, including such goods as rubber gloves, particularly medical examination and surgical gloves, male and female condoms, cervical caps and diaphragms, organ bags and containments for use in endoscopic surgery, catheter balloons and inflatable cuffs and collars, disposable barrier coverings for medical appliances and instruments, as biocompatible coverings or coatings on implantable medical appliances, such as heart pacemakers and pacemaker batteries, protective coverings for industrial equipment, particularly electronic and electrical equipment operating in demanding environments. The rubber goods molded of thermoplastic polyurethane elastomers of the present invention are hypoallergenic, free of detectable pin holes and other discontinuities, and provide excellent barrier protection to prevent contamination and the spread of disease and excellent isolation from corrosive or toxic environments. The thermoplastic polyurethane elastomers of the present invention also afford exceptional tear strength, cut resistance and puncture resistance. Elongation at break is typically greater than 500%, and may be as high as 800% or more when required. The thickness of the film of the thermoplastic polyurethane elastomers can be tailored to the requirements of a specific product, ranging from a single dipped layer as thin as about 0.5 mils, up to any thickness required through the employment of multilayer dipping operations. The thickness can be varied in different parts of the molded articles when desired, affording exceptional flexibility in the design and configuration of the articles.

Rubber gloves are an integral barrier protection employed in the medical arts and sciences generally and particularly in medical examination, surgery, and related fields to prevent the spread of disease, from patient to medical workers and vice versa. Such gloves are predominantly made of dip molded natural rubber latex, and as such are susceptible to all the shortcomings of latex molded products. In particular, the high incidence of allergic reactions and the limited resistance to cuts, tears and punctures leave the wearer vulnerable. In addition, dip molded latex has a substantial population of pin holes and pores on the order of 10 mm, which admits of the passage of mycoplasm and retrovirus particles, such as Hepatitis and AIDS viruses.

The provision of dip molded gloves of thermoplastic polyurethane elastomers suited for the medical field has long been a goal in the art. See, for example, commonly assigned U.S. Pat. No. 4,917,850 and 5,014,361. The advantages of the thermoplastic polyurethane elastomers and the desirability of their use in making rubber gloves for the medical and surgical fields is quite apparent. The procedures employed in the prior art have not resulted in economical and commercially attractive products of such materials, however, for all the difficulties and shortcomings related above.

Through the employment of the improved dip molding solutions and method of the present invention, such gloves are formed in two or more layers applied in sequential dipping steps. Such gloves have typically been formed with a film thickness of about 5 to 7 mils. In general, such thicknesses have been employed to minimize the pin holes and pores, and thinner gloves would often be desirable to improve tactile properties for the wearer. In the present invention, it is possible to make such gloves much thinner, such as 2.5 to 3 mils, for example, and still obtain the benefits of the present invention. As a result, the glove will be much more comfortable and tactile sensations far more sensitive for the wearer. Improved tactile sensitivity can be an important advantage in surgery, for example. Of course it is still possible to make the gloves in the usual thicknesses if desired.

It is also possible to mold gloves with the selective application of some layers, to provide different thicknesses in different regions of the gloves. For example, the backs of the fingers and hand can be as thick as desired, i.e., up to 5 to 7 mils or more, while the palm and tactile surfaces of the fingers are thinner, with fewer layers, i.e., about 2.5 or 3 mils, for example. The added thickness offers greater protection from needle sticks in the areas of greater thickness, while the tactile properties are optimized in the thinner regions. It is also possible to make the gloves with only the pad regions of the finger tips, or even selected finger tips with limited thickness while the rest of the structure is full thickness.

When one or more layers is selectively applied to a part but not all the surface of the form or mandrel, it should not be the first or last dip molded layer. At least the first and last layers should be full form layers to provide an encapsulation of the edges of the selectively applied layer or layers.

Finger cots are made in the same fashion as full gloves.

The use of physical barrier devices, including condoms, both male and female, cervical diaphragms and cervical caps, are widely used as a means of contraception, second only to ovulation inhibition with hormones (the pill), in frequency of use in the United States. In many countries, physical barrier devices are the only available contraceptives.

Physical barrier devices are of increasing importance in preventing the spread of sexually transmitted diseases with the increasing incidence of AIDS, and have long been advocated as the best available means to prevent infection with syphilis (*Treponema pallidum*), *Chlamydia trachomatis*, genital Herpes (Herpes Simplex, Type II), and the like.

The effectiveness of such physical barriers is limited, both in best case testing and in actual use. Pregnancy rates for condom users exhibit a lowest observed failure rate on the order of 2%, and an average typical user failure rate of 10%. Comparable failure rates are believed to apply to the spread of sexually transmitted diseases, although such matters are far more difficult to study. The limitations of such barrier devices stem from several modes of failure, but a substantial proportion are attributable to physical failure of the article, as by ripping, tearing, splitting, and other structural failures.

In the present invention, many of the causes of structural failure of barrier devices, particularly including condoms, cervical diaphragms and cervical caps, are eliminated. The dip molded multilayer films built in accordance with the present invention have improved tear strength and elongation at break than a single dipped layer of comparable thickness. Resistance to cuts and other physical challenges is greatly improved over other materials of which condoms, cervical diaphragms and cervical caps have been formed. The multilayer films are assured of unparalleled freedom from pin holes and other discontinuities, resulting in greatly enhanced product yields. The polyurethanes employed have high resistance to oxidative and ultraviolet degradation, which can be further enhanced by the use of suitable antioxidants and ultraviolet stabilizers, and have greatly improved shelf life and stability. Also of considerable importance, the improved physical properties and performance of the dip molded condoms, cervical diaphragms and cervical caps of the present invention permit the use of thinner films, enhancing comfort and tactile sensations for the wearer. Comfort and sensitivity are inadequate in condoms of conventional manufacture, leading to resistance to their use by many of those who need the protection of such articles. In the present invention it is possible to provide condoms, cervical diaphragms and cervical caps having two or three plies of 0.5 to 1.5 mils each, with a resulting thickness of 1 to 3 mils, which are equal or superior in performance to latex or conventionally formed synthetic polymer elastomer condoms, cervical diaphragms and cervical caps having a thickness of, typically, 4 to 6 mils or more. Much greater user acceptance results from the enhanced comfort and sensitivity.

When one or more layers is selectively applied to a part but not all the surface of the form or mandrel, the barrier structure can be tailored to provide the greatest thickness and strength where it is most required, e.g., the reservoir tip of condoms, while minimizing the thickness and maximizing tactile sensitivity in other less critical regions.

The male and female condoms, cervical diaphragms and cervical caps of the present invention can be formed in any suitable shape or configuration.

A male condom according to the present invention is illustrated in FIGS. 1a to 1e and FIG. 3, where a preferred form of male condom, having a reinforced end portion adapted to cover the glans and a reservoir to receive ejaculate, where male condoms are most prone to failure.

Pregnancy rates for cervical diaphragm users exhibit a lowest observed failure rate on the order of 2%, and an average typical user failure rate of 19%. The device is a pliable barrier film cup-like structure of an elastomer, sized to cover the cervix, and provided with a peripheral spring, sized and placed to fit beneath the symphysis publis anteriorly, and to engage the fornix posteriorly.

Cervical caps are less common in the United States than are cervical diaphragms, but are widely used by European women. Pregnancy rates for cervical cap users exhibit a lowest observed failure rate on the order of 2%, and an average typical user failure rate of 13%. Cervical caps differ in structure from cervical diaphragms in that the cap is of lesser diameter, and is not dependent on a fornix engaging ring to maintain its placement. The cervical cap is designed to conform precisely to the shape of the cervix when applied, and is retained in place by the surface contact in a manner similar to a suction cup.

Female condoms are a new development in the field; the first female condom has only recently been approved for the market by the Food & Drug Administration. The effectiveness of such female condoms is reported to be particularly limited, both in best case testing and in actual use. Pregnancy rates for female condom users exhibit a lowest observed failure rate on the order of 12%, and an average typical user failure rate of 25%. While these values can be expected to improve over time, as the design and use of these very new products are improved, it is apparent that considerable improvement is needed. Little is known at present about the modes of failure of existing female condoms, but we believe a significant proportion represent the same types of failures encountered with male condoms, as discussed above. In addition, a significant proportion are believed to be caused by improper insertion, with resulting damage to the condom film in critical areas. Female condoms are inserted with a tampon applicator; the film is vulnerable to damage by the applicator during insertion. Many such problems are eliminated through the employment of the materials and procedures of the present invention to enhance the physical and mechanical properties of the film. Female condoms can also benefit from the selective application of the intermediate film layers to increase the thickness of selected critical regions, and thus enhance the performance of the structure.

All the condoms, cervical diaphragms and cervical caps made in accordance with the present invention may be used in combination with the usual spermicides employed to enhance contraceptive effectiveness. Other usual additives, such as lubricants, biocides, antimicrobial agents, deodorants, fragrances, flavors, pigments and dyes, and the like may also be employed as desired. All the condoms, cervical diaphragms and cervical caps of the present invention can, of course be made in a variety of sizes, shapes and configurations to suit particular requirements and objectives. The specific design of such condoms, cervical diaphragms and cervical caps is not a part of the present invention.

The employment of endoscopicand arthroscopic surgery is a very rapidly growing field. The advantages are well known to the art and are increasingly familiar to the public as well. A very substantial number of procedures have been developed, and a significant additional number are under development. One limitation encountered in the field stems from the excision of tissues and the requirement that excised tissue be completely removed from the surgical site. For example, as many as 500,000 gall bladders are excised each year by endoscopic surgery; the excised gall bladder must be removed. Another increasingly common surgery is endoscopic hysterectomy, where the ovary is excised and must be removed. In surgery of the knee for the repair of cartledge damage, torn or debrided bits of cartledge must be removed cleanly from the joint; indeed, such removal is the very point of tile surgery in many cases. Reliable removal is quite demanding and difficult, and the use of tissue or organ bags to contain excised tissues and organs to contain and then extract such the excised material from the surgical field is increasingly the technique of choice.

A variety of organ bags have been developed, predominantly of dip molded elastomers. The use of natural rubber latex dipped bags is not favored for all the reasons set out above. The use of thermoplastic polyurethane elastomers poses all the manufacturing difficulties described above. All the significant limitations of such surgical tissue and organ bags are overcome by forming such bags in accordance with the present invention.

Such organ bags may be varied in size and shape to fit the particular requirements of a particular surgical procedure and the tissues or organs to be excised and removed. The specific design of the bags and their closures and extraction means do not themselves form a part of the present invention.

Catheter balloons and inflatable cuffs employed in angioplasty and the like are also desirably formed, in conventional configurations, by the present invention. The high degree of integrity of such structures makes them safer than dip molded catheter balloons formed by prior dip molding procedures.

Body implants devices are becoming increasingly common. Representative of these and the most common in usage is the use of heart pacemakers and their rechargeable batteries to regulate the heart beat. Such implants are designed to be encapsulated within a biocompatible polymer barrier. The long term integrity of barrier materials over many years is essential to the safety and effectiveness of such implants. Such demands are well suited to the dip molded constructions of the present invention.

It is possible to dip mold a covering over such articles using the materials and methods of the present invention, so long as the article is suitable for immersion in the dipping solution. In such cases, the entire article is encapsulated within the dip molded thermoplastic elastomer, in as many layers as required to provide the thickness and physical properties required. The implantable article serves as a mandrel or form for the dipping step, but is not subsequently removed. The result is a tight, adherent polyurethane film encapsulating the article.

In the alternative, for implants which cannot be immersed in the dipping solution, it is possible to form a bag of the appropriate shape and size on a removable form. When the bag is formed, the implant is inserted into the bag, and the opening is heat sealed, solvent welded, or otherwise tightly and permanently closed with a leak proof seal. Electrical wiring or electrical connectors may protrude though the bag. Once a tight fitting seal is formed, it is often desirable to dip the sealed article in the dipping bath to form one or more additional layers to insure the integrity of the seals.

A typical applications for such implantable devices includes forming such a covering for a heart pacemaker battery, with its associated induction coupling recharger and protruding electrical leads for connection to a heart.

There are numerous medical, surgical and dental instruments and appliances which are very difficult to clean and sterilize after use. Cross-contamination is an ever present threat to patients and medical and dental practitioners alike. A considerable effort has been devoted to the development of single use, disposable instruments and appliances to minimize such problems. For many such efforts, however, the nature of the instrument or appliance may not be amenable to cost effective production of disposable versions. In other contexts, barrier film coverings have been attempted, but with all the resulting problems discussed above.

In the present invention, highly effective, readily formed and installed and equally readily removed and discarded barrier coverings for medical, surgical and dental instruments and appliances are provided.

In one type, coverings are dip molded, as described in the present disclosure, sterilized, and the molded cover is emplaced on the sterile instrument. The openings in the cover may be sealed or, in appropriate circumstances, left open. After the appliance or instrument is used, the cover is stripped and discarded. The appliance or instrument remains sterile and clean.

In another approach, the instrument or appliance is employed as a dip molding form or mandrel. The covering is formed in situ on the surfaces of the instrument or appliance, by the application of a suitable number of layers. The instrument or appliance and its covering are sterilized prior to use. After use, the covering is stripped and discarded. In situ molding offers a number of advantages and optimal fit and protection, but requires that the dip molding operation be performed with the instrument or appliance for every use.

In either case, it will generally be preferred that the instrument or appliance be lubricated or coated with a mold release agent prior to applying the cover in order to facilitate stripping of the covering after use; in the case of preformed covers, such materials also facilitate installation of the cover. After use, the removed cover must be treated as Med Waste in either case, and handled, stored and disposed in accordance with the requirements and regulations applicable to such waste. The instrument normally remains clean and sterile (if handled under sterile conditions and procedures), and is readily resterilized and prepared for application of a new covering and another use.

A wide variety of medical, surgical and dental instruments and appliances benefit from the use of the dip molded barrier film coverings of the present invention, such as a liposuction cannula. Such cannulae are quite simple in design and construction, and represent a typical and representative example of a surgical instrument which is quite difficult to clean and sterilize after use. The cannula is typically formed of stainless steel.

The properties of the dip molded film of the thermoplastic polyurethane elastomers of the present invention will be substantially equivalent to those of comparable formulations confounded on a roll mill and formed into film by a calendar roll. As those of ordinary skill in the art will readily understand, the specific properties will vary depending on the specific polymer and the compounding ingredients and their proportions. The effect of the solvent system will be minimal on the finished properties of the product.

In the prior art techniques of dip molding thermoplastic polyurethane elastomers, in contrast, are substantially affected by the presence of significant proportions of residual solvents. Such residual solvents tend to reduce the tear strength, modulus of elasticity and tensile strength of the film, lower the Vicat softening temperature, and reduce resistance to puncture and cutting. Such diminution of important physical properties of the film are undesirable in most circumstances, and limit the strength, durability and effectiveness of molded rubber goods.

In the present invention, the molded film will generally be superior to comparable formulations formed by typical solution dip molding techniques. In particular, the tesile properties and elasticity will be greater, porosity will be nearly eliminated. The film thickness will be exceptionally uniform, at a thickness which can be closely and selectively controlled. The film will also be substantially free of any evidence of blushing, cratering, and defects caused by sensitivity to air currents and drafts during the coalescence of the film. So lone as the polymer is not heated above the Vicat softening temperature under stress, the molded shape will be retained with considerable precision. Reproducability of the molded shape is limited only by the accuracy and precision of the dimensions of the dipping forms.

In practice, it will generally be preferred to practice the invention in the following manner, which constitutes the best mode known at the present time:

A dip molding solution is formed by combining a suitable thermoplastic polyurethane elastomer, with the strong solvent component of the solvent system, and mixing under heat, at about 50° to about 60° C. until fully dissolved to form a homogeneous solution. The preferred polyurethane is that described in Example 1, below. Tetrahydrofuran is the preferred strong solvent. It is generally more rapid to dissolve the polyurethane first in the strong solvent alone.

Once the polymer is fully dissolved, the weak solvent or non-solvent component is added in an amount suitable to produce a reduced viscosity of about 800 Cps. The preferred second component is n-butanol. The n-butanol is added slowly in small increments over an hour or more and with adequate mixing to avoid precipitating the polymer. Once the viscosity is reduced, the blush resister component is added in an appropriate amount and mixed into the solution. Butyl Cellosolve (ethylene glycol monobutyl ether) is the preferred blush resistor.

Once the solution is fully formed, the viscosity is adjusted to a suitable value by the addition of additional n-butanol to a final value within the range of from about 400 to about 800 Cps.

The solution thus formed will preferably contain from about 8 to about 10 weight percent polymer solids; of the balance, about 72 to about 76 weight percent will be the tetrahydrofuran, about 16 to about 20 weight percent n-butanol, and about 6 to about 10 weight percent butyl Cellosolve.

While a leveling agent is optional in the present invention, it will be strongly preferred. Poly(dimethyl siloxane) having a molecular weight of about 600 is the preferred leveling agent. Such leveling agent may be omitted, or a non-silicone containing leveling agent employed when the invention is employed to form coverings for body implants. When the polysiloxane is employed, it will be added at a level of from about 0.1 to about 1 weight percent of the solution.

When other, optional compounding ingredients are employed, we prefer to dissolve or suspend them in a small volume of the solvent system, mixing until the components are fully wet by the solvents, and then add them to the dipping solution.

Once the dipping solution is fully formulated and ready for use, the dipping operation can proceed. The method of the operation can be understood with reference to FIGS. 1 and 2, which illustrate aspects of the method with reference to the dip molding of male condoms. It should be noted that the method is illustrated in reference to the production of male condoms because the simplicity of the structures and illustrations are an aid to clarity and understanding. Other products are equivalent, except for the shapes of the forms or mandrels employed and of the products, and the specific compounding ingredients added to the dipping solution.

In FIG. 1, a series of stages of the dipping operation are illustrated schematically. The drawings are not to scale, and are for purposes of illustration only. FIG. 1a illustrates a dipping form or mandrel, comprising a generally cylindrical shaft (1) having one rounded end (2) with a protrusion (3) formed on the tip thereof. At the opposite end the form is provided with a supporting shaft (4), on which is formed a hanger element (5), the nature and function of which are discussed below.

Figure 1D:
Figure 1C:
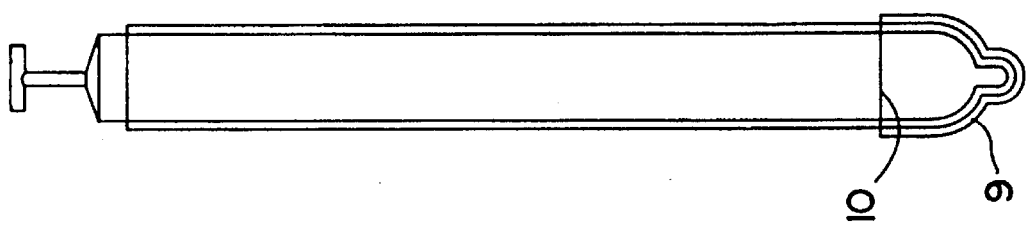
Figure 1B:
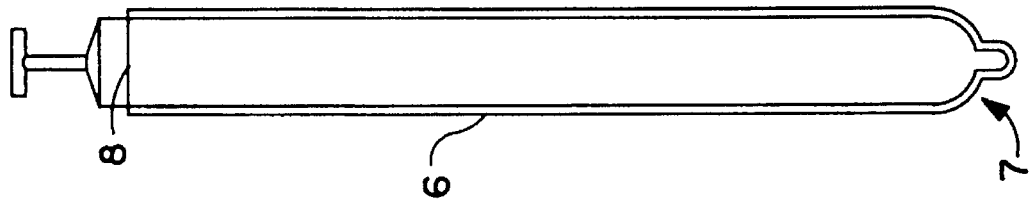
Figure 1A:
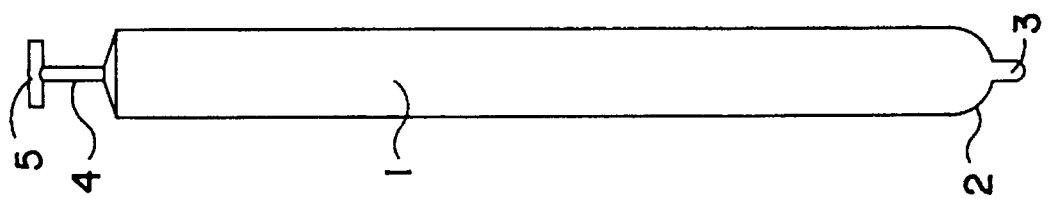

The form illustrated in FIG. 1a is coated with a suitable mold release compound over the surfaces of the shaft (1), the rounded end (2), and the tip (3), and then dipped into the dipping solution and withdrawn with a thin adherent coating of the solution; the solvent is removed by evaporation leaving a thin polyurethane film deposited on the surface of the form, as illustrated in FIG. 1b. In that view, the form is the same as in FIG. 1a, and additionally is covered with the thin polyurethane dip molded film, conforming to the shape of the form, including a shaft portion (6), and a rounded tip with a protruding reservoir (7). The film terminates on the shaft remote from the rounded tip of the form to provide an open upper margin (8). The margin (8) marks the limit of immersion of the form when dipped into the dipping solution.

FIG. 1c illustrates the formation of a second, additional tip reinforcing layer (9), formed over the initial layer illustrated in FIG. 1b, by dipping the form into the dipping solution up to the second margin (10). Again the solvent is removed by evaporation, as discussed in detail below. The second, tip reinforcing layer is integrally bonded to the underlying portions of the first layer.

The addition of a third layer is illustrated in FIG. 1d, corresponding to FIG. 1c with an additional dipping step to add a third layer (11), over the first and second layers already present. The solvent is again removed, and the third layer (11) is integrally bonded to the underlying layers.

While the third layer is partially dried and still tacky or, in the alternative, after it is dried and has been made tacky with the addition of a small amount of the strong solvent component (THF), the upper margins of the first and third layers, which are integrally bonded together, are rolled down the shaft to form the rolled upper rim (12), illustrated in FIG. 1e. In the tacky state, the rolled section (12) will permanently bond.

After the rolled section (12) is set, the completely formed condom may be subjected to any post-forming treatments. In the case of condoms, lubricants and spermicides are frequently applied. The fully formed condom is then stripped from the form, by rolling it down the shaft or by eversion. The condom is then ready for sterilization and packaging in conventional fashion.

The method is preferably carried out on a dip molding line of the general type illustrated schematically in FIG. 2. A conveyor line (20) is fitted with a plurality of the molding forms or mandrels (21), each of which conforms generally to the form of FIG. 1a in the case of condoms. Each form is attached to the conveyor line in pendant fashion, depending vertically from an articulating engagement. Dipping solution (22) is placed into a dipping vat (23), where a constant level is maintained. The solution is covered by a collection hood (24), which collects solvent vapor evaporating from the solution. The conveyor line is adjusted to descend at an incline (25) by an amount which immerses the pendant forms (21) into the dipping solution to the selected depth. After the forms are wet with the dipping solution in the bath, the conveyor line then ascends the second incline (26), which withdraws the forms (21) from the bath. The slope of the second incline (26) is adjusted and calibrated with the line speed of the conveyor line (20) to produce an appropriate rate of withdrawal of the forms from the solvent. A uniform thin coating of the dipping solution is left on the surface of each form over the surface immersed in the solvent bath.

The conveyor line (20) then carries the appended forms (21) through a heating oven (27), where the solvent is evaporated from the solution to form the thin, uniform thermoplastic polyurethane elastomer film. The solvents evaporated from the solution deposited on the forms are collected in a vapor hood (28), and passed via a conduit (29) to a solvent recovery system, not shown.

The forms (21) exiting the drying oven (27) are collected and removed from the conveyor for further processing.

While only a single dipping operation is illustrated in FIG. 2, it should be understood that it is preferred in most cases to dip the form multiple times, to form a multilayered dip molded product. Plural dipping operations can be performed with the single bath arrangement shown in FIG. 2 by returning the forms to the beginning and running them through the dipping line a second time, with the dipping solution at the same or a different level. A second dip and drying operation may be effected by removing the forms from the conveyor when they pass out of the drying oven, moving them back to the beginning, and rehanging them on the conveyor line (20). It is also possible, and more desirable in such cases, to let them remain on a continuous conveyor line, which is provided with a return to the dip bath. For volume production, it is preferred to employ a series of dipping baths (23), each with its own inclines (25) and (26), adjustable to provide the appropriate depth of immersion, and each followed by its own drying oven (27). A single continuous conveyor (20) carries the forms (21) through each dipping bath and drying oven in turn, producing multiple layers of the polyurethane elastomer film in each of the multiple dipping operations. Such an operation provides a complete dip molding operation at a maximum production rate and a minimum of handling and labor.

Uniformity and high quality of the dip molded product are assured by monitoring and controlling the important parameters of the operation. Paramount among these are the level of the solution in the dipping baths and the temperature, viscosity and polymer concentration of the solution in each bath. Also important are the rate of withdrawal of the forms from the solution, and the drying temperature in each oven.

The present invention is illustrated in the following specific examples, which are intended for the guidance of those of ordinary skill in the art and not as limitations on the scope of the invention.

EXAMPLE 1

A thermoplastic polyurethane elastomer was prepared by adding 122 parts by weight of dicyclohexyl methane diisocyanate to a mixture of 150 parts by weight of polytetramethylene ether glycol having a molecular weight of 1,000, 24 parts by weight of 1,4-butane diol, 3 parts by weight of an antioxidant, tetrakis[methylene)3,5-ditertiary butyl-4-hydroxyhydrocinnamate)]methane, 0.5 parts by weight of ethylene-bis-oleamide and 0.03 parts by weight dibutyl tin dilaurate. The components were mixed and deaerated until all entrained gases were removed, and the mixture was spread in a thin layer of about 1 mm, and reacted at 110° C. for three hours under a nitrogen atmosphere. The resulting polymer sheets were then cut into small pellets.

Ten parts by weight of the polyurethane pellets were combined with 74 parts by weight tetrahydrofuran, and mixed at 50° C. for three hours. A homogeneous, viscous solution was produced. The solution was thinned by gradually mixing in small additions of n-butanol until the viscosity reached 800 Cps. Eight parts by weight of ethylene glycol monobutyl ether and 0.65 parts by weight of a poly(dimethyl siloxane) having a molecular weight of 600 were added and thoroughly mixed into the solution. The viscosity of the solution was adjusted with n-butanol to a final viscosity of 650 Cps. A total of 18 parts by weight of n-butanol were added to the solution.

One hundred male condoms are dip molded from the solution by the procedure described above, as illustrated in FIGS. 1 and 2; the condoms correspond to the illustration of FIG. 3.

The condoms are subjected to testing as follows:

The wall thickness is measured on the shaft (two ply) region and in the tip (three ply) region. The film thickness is found to be 2.89 mils, +/–0.14 mils in the shaft and 4.24 mils, +/–0.18 mils at the tip.

Elongation at break is measured on twenty five of the condoms, and is 725%, +/–12%.

Twenty five condoms are filled with 1,000 ml water at room temperature, and held for five minutes. None of the condoms leak or burst.

Twenty five condoms are filled with air at 5 psig and held at that pressure for five minutes. None of the condoms leak or burst.

Twenty five condoms are subjected to accelerated aging by exposure to UV light in an oxygen atmosphere at 90° C. for four days. The aged condoms are then subjected to the water test with 1,000 ml for five minutes. None of the condoms leak or burst.

While the present invention has been discussed with reference to thermoplastic polyurethane polymers, which are generally preferred for the medical appliance uses of greatest interest, it is also possible to employ the method of the present invention with other thermoplastic elastomers, such as the syrene-based block copolymers, such as Krayton® (Shell), acrylic thermoplastic elastomers, and polyurethane alloys with other polymers. Those of ordinary skill in the art will be able to select appropriate solvents adapted and best suited for these additional thremoplastic elastomers from the information available in the literature given the guidance and objectives defined in the present disclosure.

Those of ordinary skill in the art will readily be able to adapt the foregoing description and exemplary guidance in the formation of suitable rubber goods from polyurethane elastomers. The specification, description and examples should not be considered as limiting on the scope of the invention, which is intended to be defined in the following claims. The scope of the invention is properly to be construed in terms defined in the claims.

What is claimed is:

1. The method of dip molding polyurethane elastomers comprising:
    A. forming a dipping solution comprising:
        i. a polyurethane elastomer;
        ii. a first solvent component which is at least one strong solvent for said polyurethane elastomer;
        iii. a second solvent component which is at least one non-solvent or non-polar or low polarity weak solvent for said polyurethane elastomer, whereto said second solvent component is freely miscible with said first solvent component;
        iv. a third solvent component which is at least one blush resistor which limits the rate of evaporation of said first solvent component and said second solvent component and which limits the absorption of water vapor into said composition;
        v. wherein said polyurethane is homogeneously dissolved in said solvent to form a solution having a viscosity in the range of from about 400 to about 800 cP;
    B. dipping a shaped form into said solution to wet the surface of said form;
    C. withdrawing said form from said solution to deposit a coating of said solution on the surface thereof, said coating having a thickness of from about 0.5 to 1.5 mils;
    D. drying said coating to form a continuous, non-porous solid polyurethane elastomer film having a thickness of from about 0.5 to about 1.5 mils on the surface of said form;

E. repeating steps B, C, and D at least one additional time the continuous, non-porous solid polyurethane elastomer film has at least two of said thicknesses;

F. stripping from said form said continuous, non-porous solid polyurethane elastomer film conforming to the shape of said form.

2. The polyurethane elastomer dip molding method of claim 1 wherein said first solvent component is a member selected from the group consisting of tetrahydrofuran, N-methylpyrrolidone, dimethyl acetamide, dimethyl formamide, methyl ethyl ketone, methylene chloride and mixtures thereof.

3. The polyurethane elastomer dip molding method of claim 1 wherein said second solvent component is a member selected from the group consisting of non-polar aliphatic and aromatic hydrocarbons having solubility parameters less than about 4.3, or greater than about 5.3.

4. The polyurethane elastomer dip molding polyurethane elastomer composition of claim 3 wherein said second solvent component solubility parameter is less than about 4.0 or greater than about 5.5.

5. The polyurethane elastomer dip molding method of claim 1 wherein said second solvent component is n-butanol.

6. The polyurethane elastomer dip molding method of claim 1 wherein said third solvent component is a member selected from the group consisting of glycol ethers and esters and mixtures thereof having a boiling point of about 20° C. to about 225° C.

7. The polyurethane elastomer dip molding method of claim 6 wherein said third solvent component has a boiling point of about 100° C. to 200° C.

8. The polyurethane elastomer dip molding method of claim 1 further comprising a leveling agent of poly (dimethyl-siloxane) with a molecular weight of about 250 to about 1,000.

9. The polyurethane elastomer dip molding method of claim 1 wherein said polyurethane elastomer is dissolved in said solvent system in an amount of from about 6 to 12 percent by weight of the dip molding solution.

10. The polyurethane elastomer dip molding method of claim 1 wherein said polyurethane elastomer is dissolved in said solvent system in an amount of from about 8 to 10 percent by weight of the dip molding solution.

* * * * *